United States Patent [19]

DiFoggio et al.

[11] Patent Number: 4,787,983

[45] Date of Patent: Nov. 29, 1988

[54] METHOD FOR DETERMINING THE AMOUNT OF OIL IN A SPONGE CORE

[75] Inventors: Rocco DiFoggio; William E. Ellington; Kailash C. B. Dangayach, all of Houston, Tex.

[73] Assignee: Shell Oil Company, Houston, Tex.

[21] Appl. No.: 122,622

[22] Filed: Nov. 17, 1987

Related U.S. Application Data

[63] Continuation of Ser. No. 814,334, Dec. 27, 1985, abandoned.

[51] Int. Cl.⁴ ............................................. B01D 15/08
[52] U.S. Cl. .................. 210/656; 73/61.1 C; 73/153; 166/250
[58] Field of Search ............... 73/61.1 C, 153; 166/250; 210/635, 656–659

[56] References Cited

PUBLICATIONS

Hawley, The Condensed Chemical Dictionary, Eighth Edition, Van Nostrand, New York, 1971, pp. 255, 368, & 402.
Dowdco Sponge Coring Brochure, Midland, Texas, pp. 1–8, 1981.

Primary Examiner—Ernest G. Therkorn

[57] ABSTRACT

The oil lost by the core sample and captured by the sponge during sponge coring is extracted from the sponge using a solvent selected from the group consisting of cycloalkanes, ethers, and freons.

15 Claims, 3 Drawing Sheets

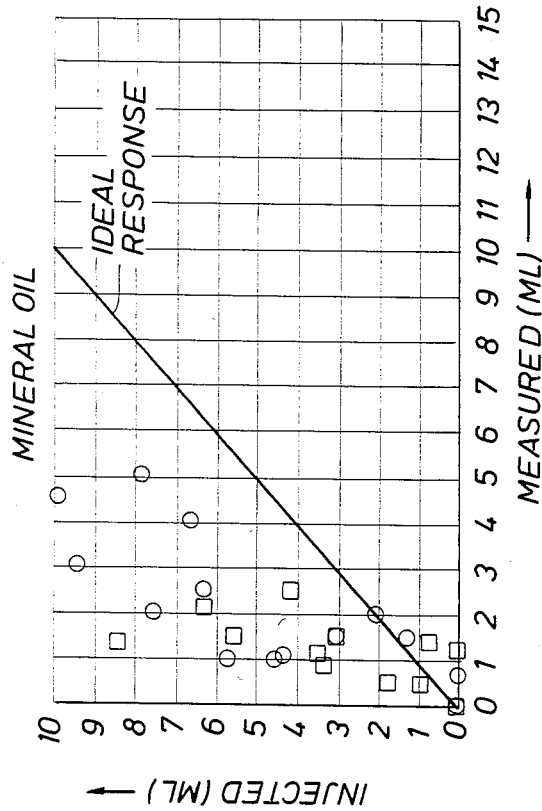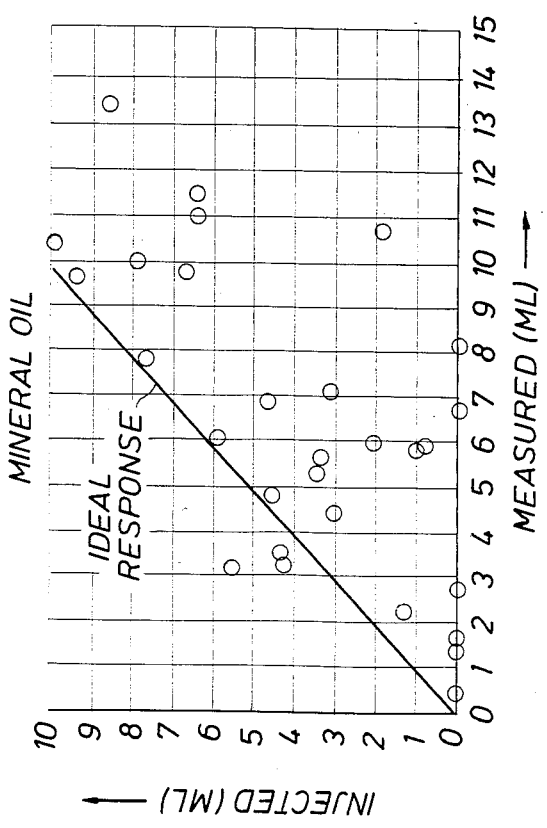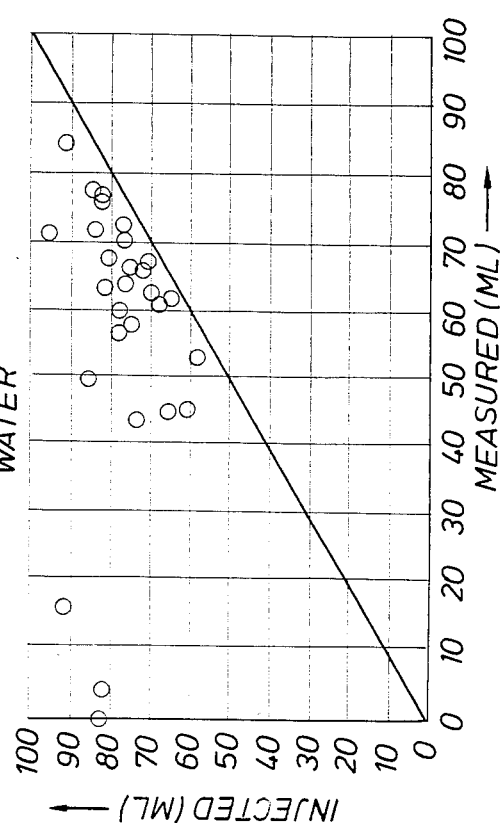

METHOD FOR DETERMINING THE AMOUNT OF OIL IN A SPONGE CORE

This is a continuation of application Ser. No. 814,334, filed Dec. 27, 1985, now abandoned.

BACKGROUND OF THE INVENTION

The present invention relates to the exploration and production of petroleum from earth formations, and more particularly to methods for determining the amount of oil present in such a formation.

In the petroleum industry, one of the most valuable and informative techniques for determining the characteristics of an earth formation located well below the surface, and the nature of the fluids which it may contain, is to remove and bring a portion of the formation to the surface for analysis. This is most commonly done by "coring" the formation. Of course, physical conditions in the formation are substantially different from those at the surface: pressures and temperatures are ordinarily enormously elevated over surface conditions. Therefore, fluids and gases present in porous rock samples very often evolve from those samples as they are recovered from the formation. To the extent that such liquids and gases are lost, the accuracy of the evaluation of the formation production potential is accordingly impaired.

To control this problem, a technique called "pressure coring" is often employed. With pressure coring, the core is contained at substantially its original formation pressure until a proper analysis can be made. Pressure coring, while overcoming such fluid loss problems to a great extent, is quite expensive (for example, $100,000-$200,000 for a single coring operation)

Recently, a technique called "sponge coring" has been developed. It is substantially less expensive than pressure coring. In sponge coring, the core is surrounded by a polyurethane sponge lining on the inner barrel of a conventional core barrel. As the core is brought to the surface, any oil that bleeds from the core (and this can be as much as 50% of the original core fluid) is caught and retained by the sponge liner. An analysis is then made of the fluids (oil and water) captured by the sponge, and the analysis of the core adjusted accordingly.

The importance of coring in the production of petroleum has recently been increasing as more and more secondary and tertiary recovery is being made of petroleum reserves. In a formation undergoing primary production, the original reservoir fluids are little altered from their condition for the last several thousand years. They may migrate as the oil is produced, but their properties are little changed. However, when fluids and/or other compounds are injected into a formation to stimulate its production, the nature of the connate fluids is accordingly altered, sometimes to a very substantial extent. When this occurs, the more traditional well bore logging tools may be unable to provide further useful information. In all too many instances, the only way to determine how much oil is left, and thus whether it can be produced economically, is to go down there and take a core sample.

It will therefore be appreciated that the analysis of the oil content of the core sample can be critically important. The final true residual oil saturation of a formation is a determination that can make or break a multimillion dollar enhanced recovery project. Hence, the considerable interest in sponge coring, which can cost as little as only 20-30% as much as pressure coring.

Currently, a major problem with sponge coring is that, curiously, the industry has not been able to make consistently reliable measurements of the amount of oil in the sponge, to the degree of accuracy necessary for meaningful reservoir analysis. Many service companies have tried, and are continuing to try, to measure the oil in the sponge either by extracting the oil with solvents or squeezing the sponge in a vice, or both. However done, usually not all the oil is removed, while often some of the sponge is dissolved instead. Thus, unextracted oil is not counted while extracted sponge is erroneously counted as oil. This is demonstrated, for example, in FIGS. 2, 3, and 4, which are existing (prior art) results of blind tests sent to several different service companies. In these tests, sponge samples were prepared by saturating first with deionized water and then spiking with a known volume of mineral oil. The results reported back by the service companies graphically illustrate the problems with current technology.

For example, in FIG. 2, a three-step mechanical solvent extraction technique was employed. Heat was used in the first step, followed by the administration of dichloromethane solvent, then repeated squeezing and draining in a hydraulic press. The solvent was then driven off.

In FIG. 3, two different methods were used, one being a two-step process involving a mechanical solvent extraction of the sponge and distillation of the extracted fluid, and the other being a two-step process involving mechanical extraction of the sponge followed by retorting the sponge. Since no apparent systematic differences were noted, data for both methods are combined in FIG. 3.

FIG. 4 illustrates the results of a process in which the sponge is first placed in a steel container with dichloromethane solvent, and then repeatedly compressed with the addition of more solvent until the drained solvent is clear. The solvent with oil is then separated from water and the solvent subsequently removed. The results at this point are then corrected by repeating the process with a sponge spiked with a known weight of oil and comparing the results.

As can be seen from the drawings, none of these techniques yields an accurate or precise determination of the injected oil volumes. Accordingly, a substantial need still remains for a method for extracting oil from the sponge of a sponge coring operation which will accurately reflect the actual amount of oil captured by the sponge, leaving the sponge itself substantially unaffected. Preferably, a solvent should be found which will be gentle on the polyurethane sponge, neither swelling nor dissolving it, and which will be a good solvent for all the components of crude oil, including heavy resins, waxes, and asphaltenes. Preferably, the solvent should have a low boiling point so that it can be simply evaporated or boiled off to leave only the volume of crude oil which was contained in the sponge. Alternatively, a rapid and simple analytical technique for the solution of solvent and oil should be provided so that the volume of the oil which was captured by the sponge can be readily and rapidly determined.

SUMMARY OF THE INVENTION

Briefly, the present invention meets the above needs and purposes with a rapid, uncomplicated and economical method for determining the oil saturation of an earth formation using sponge coring, wherein the oil is readily extracted from the polyurethane sponge without substantially affecting the sponge. In particular, it has been discovered, as suggested above, that the solvents being currently used by practitioners in the art are not satisfactory. Contrary to some expectations, it has been discovered that cycloalkanes, ethers, and freons, meet the above above-noted criteria. That is, these solvents readily extract the oil from the sponge without affecting the sponge itself. Thus, virtually all of the oil is removed, while none of the sponge material is removed. The resulting solution of oil dissolved in solvent is then analyzed. Presently, the preferred method for extracting the oil is to process the sponge in a Soxhlet extractor, although other methods, such as squeezing and relaxing the sponge in a solution of the selected solvent, and so forth, can of course be considered.

Following extraction of the oil, the amount of oil which has been dissolved into the solvent is then determined. As suggested above, this can be performed simply by evaporating or boiling off the solvent. Another method taught by the present invention, and which produces extremely rapid analytical results, is to compare the solvent solution directly with a similar standard solution, preferably made up of the selected solvent and oil from the formation, or oil similar thereto. In this method, the test core sponge oil is removed from the sponge with a predetermined known quantity of the solvent, so that the measured concentration of oil in the predetermined quantity of solvent will be a meaningful indication of the total amount of oil removed. The test solution of oil removed from the sponge is then compared with the standard solution using known analytical techniques such as near infra-red spectroscopy or supercritical fluid chromatography. The former (near infra-red spectroscopy) is attractive because it can be used to quantify the number of CH bonds. For example, with a freon solvent, there are no CH bonds, so the oil concentration can be readily determined. Similarly, supercritical fluid chromatography looks only at the aromatics, which are not present in the solvents taught in the present invention.

It is therefore an obJect of the present invention to provide a substantially improved method for determining the amount of oil in a sponge core; such a method in which the oil can be removed from the sponge without substantially affecting the sponge; in which the oil is extracted from the sponge by dissolving the oil in a solvent selected from the group consisting of cycloalkanes, ethers and freons; in which a determination is then made of the amount of oil dissolved in the solvent; in which such a determination can be made by evaporating the solvent or analyzing the solvent solution by comparing it with a standard solution; in which the comparison can be made using near infra-red spectroscopy or supercritical fluid chromatography; and to accomplish the above objects and purposes in an inexpensive, uncomplicated, versatile, economical and reliable method readily suited to the widest possible utilization in the analysis of oil bearing earth formations by sponge coring methods.

These and other objects and advantages of the invention will be apparent from the following description, the accompanying drawings, and the appended claims.

BRIEF DESCRIPTION OF THE DRAWINGS

FIGS. 2A and 2B are graphical illustrations showing the results of current (prior art) measurement methods used to determine the amount of oil in the sponge;

FIGS. 3A and 3B are graphical illustrations showing the results of another current measurement method used to determine the amount of oil in the sponge;

DESCRIPTION OF THE PREFERRED EMBODIMENTS

Figure 1:
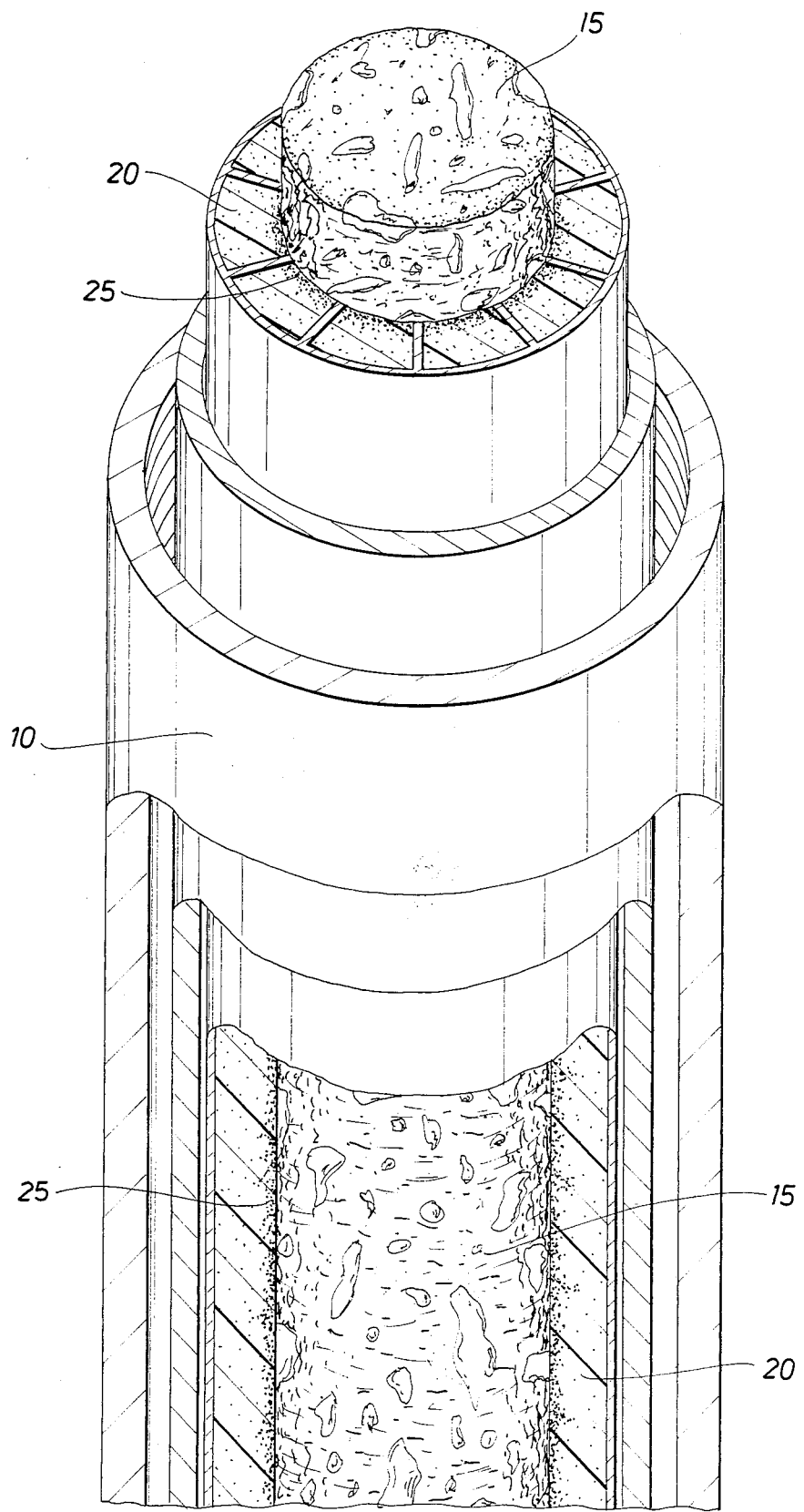
FIG. 1 is a somewhat figurative illustration showing a sponge coring tool.

With reference to the drawings, the new and improved method for determining the amount of oil in sponge core will be described. FIG. 1 shows a coring tool 10 having a formation core sample 15 therein. Sample 15 is surrounded in known fashion by polyurethane sponge 20 to capture and retain any formation fluids which might bleed from sample 15 as it is brought to the surface. To analyze the formation sample properly, the amount of fluid in the core 15 and the amount of fluid captured by sponge 20 are then summed.

According to the present invention, the oil 25 in sponge 20 is removed from the sponge by first placing the sponge in a suitable extractor. In the preferred embodiment a Soxhlet extractor is used, although other suitable extractors, and/or mechanical methods for washing the sponge with the solvent, may be used as appropriate. The solvent to be used according to the present invention is selected from the group consisting of cycloalkanes, ethers, and freons. These readily dissolve all the constituents of the crude oil, while leaving the polyurethane sponge virtually unaffected.

According to the present invention, the amount of oil which has thus been dissolved into the solvent is then determined. These solvents are readily evaporated or boiled off, or alternatively a measured amount of solvent can be initially used, and then the concentration of the oil in the solvent readily and quickly determined. According to the present invention, such a determination can be made by comparing the amount of oil, that is, the oil concentration in the solvent, with a standard solution of oil in another quantity of the same solvent. According to circumstances, this comparison can be accomplished using near infra-red spectroscopy (e.g., when the solvent is a freon), or supercritical fluid chromatography (e.g., when the solvent contains CH bonds). Presently preferred solvents include cyclohexane, cyclopentane, diethyl ether, and freon-11. Freon-114, freon-C318, and cyclobutane are also believed, among others, to be particularly attractive according to the teachings herein.

Figure 5A:
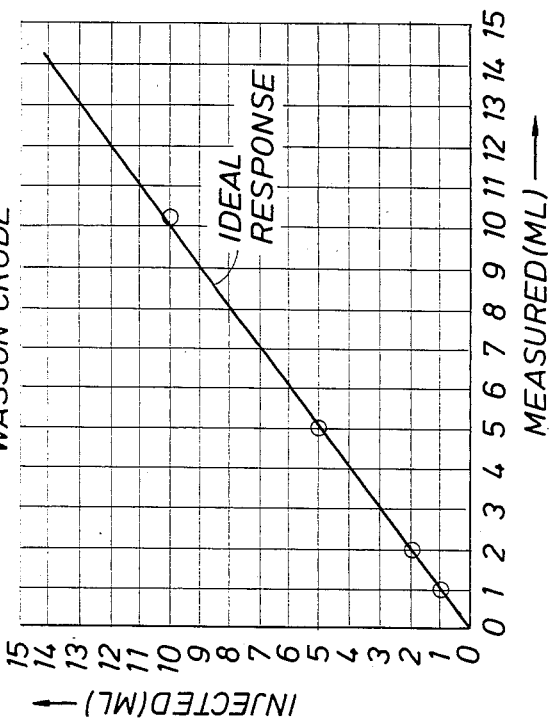
FIGS. 5A and 5B are similar graphical illustrations showing preliminary results of measurements performed according to the present invention.
Figure 5B:
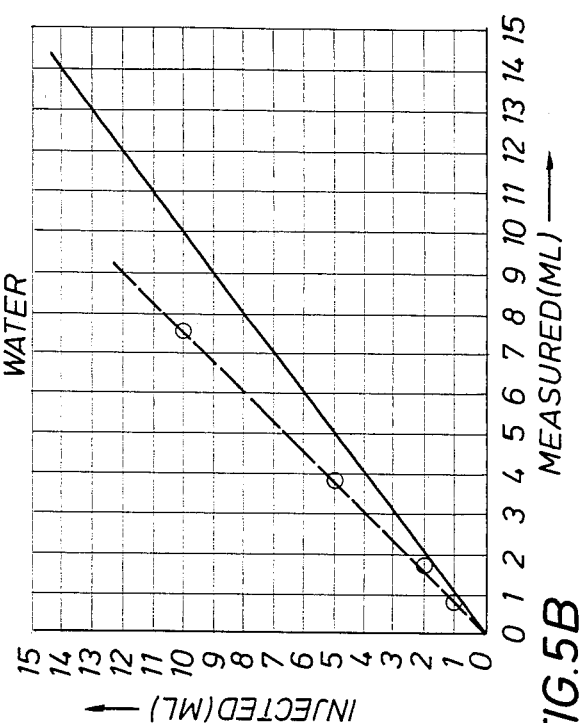
Figure 4A:
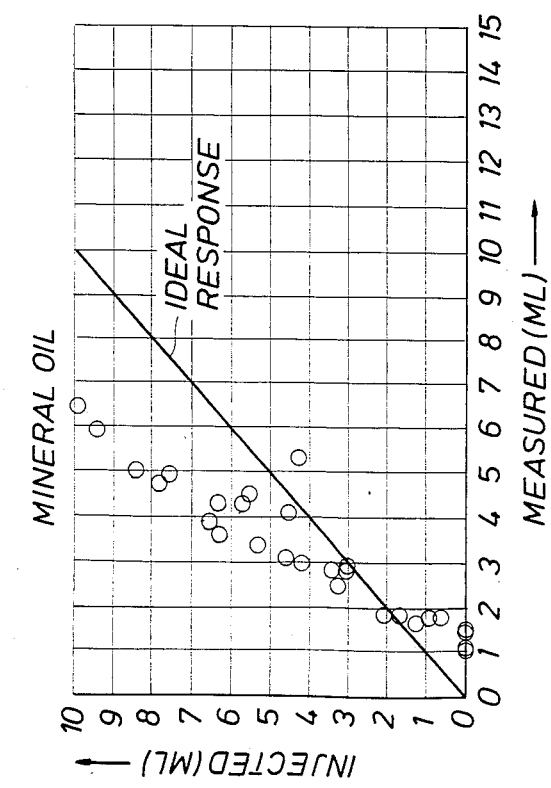
FIGS. 4A and 4B are graphical illustrations showing the results of still another current measurement method used to determine the amount of oil in the sponge.
Figure 4B:
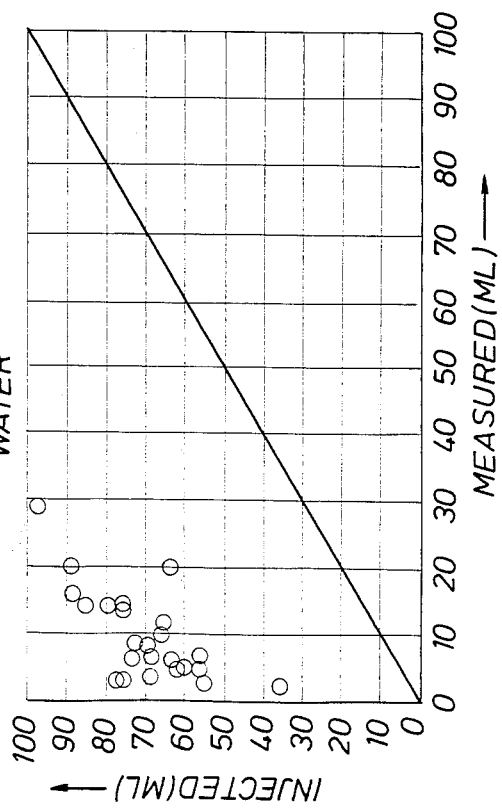

Referring to FIGS. 5A and 5B, the results of simple tests using mechanical squeezing and relaxing of a test sponge in a freon-11 solvent are shown. As may be seen, after evaporating the solvent, the results were far better than those shown in FIGS. 2–4.

As may be seen, therefore, the present invention has numerous advantages. It is extremely rapid, accurate, and easy to perform. It solves a substantial and pressing problem in the art by enabling virtually all the crude oil to be removed from the sponge without affecting the sponge. Thus, all the oil—and only oil—is measured. The invention is thus accurate, versatile, reliable and suited to the widest possible utilization in the analysis of petroleum reserves in oil bearing earth formations.

While the methods herein described constitute preferred embodiments of this invention, it is to be understood that the invention is not limited to these precise methods, and that changes may be made therein without departing from the scope of the invention.

What is claimed is:

1. For use in determining the oil saturation of an earth formation by means of sponge coring, a method for extracting oil from the sponge without substantially affecting the sponge, comprising:
    (a) extracting the oil from the sponge by dissolving the oil in a solvent selected from the group consisting of cycloalkanes, ethers, and freons, and
    (b) determining the amount of oil dissolved into the solvent by evaporation of the solvent, by near infra-red spectroscopy, or by supercritical fluid chromatography.

2. The method of claim 1 further comprising extracting substantially all the oil from the sponge.

3. The method of claim 1 wherein said step of dissolving the oil further comprises using a predetermined quantity of the selected solvent.

4. The method of claim 3 wherein said step of determining the amount of oil dissolved into the solvent further comprises:
    (a) preparing a standard solution of oil in another quantity of the selected solvent, and
    (b) comparing the concentration of the oil extracted from the sponge in the predetermined quantity of solvent with the concentration of the oil in the standard solution.

5. The method of claim 1 further comprising selecting cyclohexane as the solvent.

6. The method of claim 1 further comprising selecting cyclopentane as solvent.

7. The method of claim 1 further comprising selecting diethyl ether as the solvent.

8. The method of claim 1 further comprising selecting freon-11 as the solvent.

9. The method of claim 1 further comprising selecting freon-114 as the solvent.

10. The method of claim 1 further comprising selecting freon-C318 as the solvent.

11. The method of claim 1 further comprising selecting cyclobutane as the solvent.

12. For use in determining the oil saturation of an earth formation by means of sponge coring, a method for extracting oil from the sponge without substantially affecting the sponge, comprising:
    (a) extracting substantially all the oil from the sponge by dissolving the oil in a predetermined quantity of cyclopentane, and
    (b) determining the amount of oil dissolved into the solvent by:
        (i) preparing a standard solution of oil in another quantity of the selected solvent, and
        (ii) using supercritical fluid chromatography, comparing the concentration of the oil extracted from the sponge in the predetermined quantity of solvent with the concentration of the oil in the standard solution.

13. For use in determining the oil saturation of an earth formation by means of sponge coring, a method for extracting oil from the sponge without substantially affecting the sponge, comprising:
    (a) extracting the oil from the sponge by dissolving the oil in a solvent selected from the group consisting of cycloalkanes, ethers, and freons, and
    (b) determining the amount of oil dissolved into the solvent by evaporating the solvent from the oil.

14. For use in determining the oil saturation of an earth formation by means of sponge coring, a method for extracting oil from the sponge without substantially affecting the sponge, comprising:
    (a) extracting the oil from the sponge by dissolving the oil in a predetermined quantity of a solvent selected from the group consisting of cycloalkanes, ethers, and freons, and
    (b) determining the amount of oil dissolved into the solvent by:
        (i) preparing a standard solution of oil in another quantity of the selected solvent, and
        (ii) comparing the concentration of the oil extracted from the sponge in the predetermined quantity of solvent with the concentration of the oil in the standard solution, using near infra-red spectroscopy to determine the concentrations of the oil.

15. For use in determining the oil saturation of an earth formation by means of sponge coring, a method for extracting oil from the sponge without substantially affecting the sponge, comprising:
    (a) extracting the oil from the sponge by dissolving the oil in a predetermined quantity of a solvent selected from the group consisting of cycloalkanes, ethers, and freons, and
    (b) determining the amount of oil dissolved into the solvent by:
        (i) preparing a standard solution of oil in another quantity of the selected solvent, and
        (ii) comparing the concentration of the oil extracted from the sponge in the predetermined quantity of solvent with the concentration of the oil in the standard solution, using supercritical fluid chromatography to determine the concentrations of the oil.

* * * * *